United States Patent [19]

Mack et al.

[11] 4,058,895

[45] Nov. 22, 1977

[54] DENTAL ARTICULATOR

[75] Inventors: Heinz Mack; Günter Singer, both of Munich, Germany

[73] Assignee: Heinz Mack, Munich, Germany

[21] Appl. No.: 666,395

[22] Filed: Mar. 12, 1976

[30] Foreign Application Priority Data

Mar. 15, 1975 Germany .............................. 2511388
Nov. 15, 1975 Germany .............................. 2551189

[51] Int. Cl.² .......................................... A61C 19/02
[52] U.S. Cl. ........................................................ 32/32
[58] Field of Search ........................................... 32/32

[56] References Cited

U.S. PATENT DOCUMENTS 3,478,431 11/1969 DePietro .................................. 32/32
3,905,112 9/1975 Swanson .................................. 32/32

Primary Examiner—Robert Peshock
Attorney, Agent, or Firm—Larson, Taylor and Hinds

[57] ABSTRACT

This invention relates a dental articulator comprising substantially a lower frame portion with means for securing the mounting plate for the lower jaw model and a supporting platform for the incisor guide pin, a vertical frame portion rigidly connected to the lower frame portion and having two balls serving as condyles which are mounted on two supporting stems, and an upper frame portion with the two radially rotatable ball sockets serving as fossae and including a rear ball guiding means and an inner ball guiding means angularly adjustable relative to the rear ball guiding means, the bearing shaft, the means for securing the mounting plate for the upper jaw model, and an adjustable incisor guide pin, in which the inner ball guiding means angularly adjustable relative to the rear ball guiding means constitutes an exchangeable, optionally grindable segment of a circle bearing against the circular inner wall of the ball socket, and a lockable slide serves to lock the ball in the corner formed by the rear ball guiding means, the angularly adjustable inner ball guiding means, and the upper ball guiding surface, which slide is arranged opposite or diagonally opposite the corner formed by the rear ball guiding means and the angularly adjustable inner ball guiding means such that after locking the end of the slide rests on the lower half of the ball.

13 Claims, 18 Drawing Figures

DENTAL ARTICULATOR

The present invention relates to a dental articulator which substantially comprises a lower frame portion with the means for securing the mounting plate for the lower jaw model* and a supporting platform for the incisor guide pin, a vertical frame portion rigidly connected to the lower frame portion and including two balls serving as condyles which are mounted on two supporting stems, and an upper frame portion with the two radially rotatable ball sockets serving as fossae and including a rear and an inner ball guiding means, the latter angularly adjustable relative to the rear ball guiding means, the bearing shaft, the means for securing the mounting plate for the upper jaw model,** and an adjustable incisor guide pin.
* maxilla cast
** mandible cast Dental articulators serve to simulate the motions of the lower jaw; by individual adjusting possibilities the course of the limiting lines of motion can be simulated. The requires mounting of the jaw models in the articulator in line with the proper coordinates, i.e. in proper relation to the skull.

Dental articulators of the initially described type have been known, e.g. the so-called Arcon articulators. It is a shortcoming of all articulators of the Arcon type that the ball cannot be locked in the ball socket. It is a further disadvantage that the angularly adjustable inner ball guiding means is distorted or deformed during use by the compressive forces acting thereon. Moreover, it has proved to be disadvantageous that in said Arcon type articulators the ball contacting faces cannot be watched, and the guidance of the bearing shaft of the ball socket is lost when the clamping screw for adjusting the horizontal angle of inclination is loosened. Moreover, it has been found that the supporting stems with the balls serving as condyles on the vertical frame connected to the lower frame do not have identical spacing values when manufactured on an industrial scale. Furthermore, handling is made difficult by mounting plates which are soiled on the critical contact surface.

Therefore, it is the object of the present invention to provide a dental articulator which does not have the above mentioned drawbacks.

According to the invention, this object is realized in that the inner ball guiding means adjustable angularly relative to the rear ball guiding means constitutes an exchangeable and optionally grindable segment of a circle bearing against the circular inner wall of the socket, and for fixing the ball in place a lockable slide is provided in the corner formed by the rear ball guiding means and the angularly adjustable inner ball guiding means and the upper ball guiding surface, which slide is positioned opposite or diagonally opposite the corner formed by the rear ball guiding means and the angularly adjustable inner ball guiding means such that after locking the end of the slide rests against the lower half of the ball.

Hence, it is a main feature of the invention that the inner ball guiding means angularly adjustable relative to the rear ball guiding means has the form of a segment of a circle whose radius of curvature extends around the center of the ball, and thus the angle of the bearing face relative to the ball is variable without the position of the ball being varied. The angle of contact may be read from an entrained dial on the upper side of the ball socket. Moreover, the segment may be locked in the desired angular position. The contact pressure exerted by the ball is transmitted from the ball contacting surface of the segment via the arcuate outer wall of the segment to the circular inner wall of the ball socket. Thus the axial pressure loads do not result in under- or over-adjustment. The rear ball contacting surface may have an angle of inclination of less than 90° with respect to the side of the ball.

If desired, also the rear ball guiding means may, of course, be angularly adjustable like the inner ball guiding means and constitute an exchangeable and optionally grindable segment of a circle bearing against the circular inner wall of the ball socket.

The ball socket with the bearing shafts and the rear ball guiding means are preferably manufactured by introducing a metallic bearing shaft provided with a metal frame into a forming tool corresponding to the desired ball socket shape and then surrounding it with a preferably glidable plastic material, e.g. by injection molding or casting. Suitable synthetic resins include both filled and unfilled plastics, especially fiber-reinforced plastics, e.g. glass fiber or carbon fiber-reinforced polyamides, polyimides or polytetrafluoroethylenes. In cases where the synthetic resins per se already possess the desired mechanical properties, the frame for inner reinforcement may be omitted.

Preferably the metal frame to be covered by injection molding has a recess in its transverse axis which is left open also during injection molding to provide an inspection window. The inspection window permits direct observation of the ball contacting points at the rear ball guiding means and the upper ball guiding surface.

The angularly adjustable inner ball guiding means preferably consists of the same plastic material as the ball socket. Of course, all parts may consist of cast or turned, pressed or otherwise worked metal parts.

Another significant main feature of the invention in the lockable slide for fixing the ball in the corner formed by the rear ball guiding means and the angularly adjustable inner ball guiding means and by the upper ball guiding surface. The slide is arranged such that after being locked in place it bears against the lower ball half thereby urging the ball into the corner formed by the two ball guiding means and the upper ball guiding surface. This fixing is place has the purpose of reliably connecting the upper frame of the lower frame in a specific and reproducible position, while nevertheless permitting rotation about the transverse axis (hinge axis).

The lockable slide may have various configurations, e.g. it may be designed as a wall, a wedge, or as a cylindrical pin; preferably the end of the slide, i.e. the portion of the slide that comes to bear against the ball surface, is oblique or concave.

However, the slide has not only the above described locking function, it also has the purpose, after having been locked in place, to serve as a point of separation in case of overload. This is a further essential aspect of the invention.

Another essential feature of the invention is the downwardly extending part of the upper frame which is designed as a transverse block and in which the bearing shafts of the two ball sockets are locked after having been accordingly adjusted in the bearing bores extra provided for this purpose and serving as bearing guides. Care has to be taken that the bearing bores for the bearing shafts are located a certain distance below the plane of the upper frame. This provides sufficient space for the control stand of the upper jaw model between the reference plane and the upper frame. Moreover, owing to the bearing bores of the invention the bearing shaft guidance is not lost upon release of the locking mechanism when the desired angle of inclination is adjusted by rotation of the bearing shaft about the longitudinal axis, so that in this way the desired inclination of the ball guiding means may be easily adjusted. The angle of inclination may be read from a dial.

On principle, the bearing shaft may be locked in the bearing bore by a simple screw locking means. However, since in such a case the locking screw must be pulled very tight, which would damage the bearing shaft, it is preferred for the purposes of this invention to lock the bearing shaft in place by means of a cylindrical clamping element. The cylindrical clamping element has a bore in the longitudinal axis which is somewhat wider than the diameter of the threaded shank of the locking screw extending through the clamping element. Moreover, at the end contacting the bearing shaft the clamping element is designed perpendicularly to the longitudinal axis such that a concave area is formed whose radius of curvature conforms to that of the bearing shaft. By this measure the clamping element bears against the shaft with a larger area as the locking screw is tightened.

However, in lieu of the concave surface the clamping element may also have a wedge-shaped surface; yet, then the locking effect is confined to linear contact. When the clamping element is conical — which is also possible according to the invention — the locking effect is confined to point contact which substantially corresponds to the simple screw-type locking.

According to the invention, the two ball sockets may be exchanged for extensible calibrated shafts or millable or finally shaped element blocks, or such blocks that may be finally molded with plastic compositions whose precise alignment is achieved by an additional pin or a jaw.

According to the invention, the vertical frame consists of the supporting pillars with crossbar. Both the supporting pillars and the crossbar are adapted for swivelling motion and are rigidly connected in a gauge, e.g. by bolts. In this way the bores and threads for receiving the ball supporting stems are always equally spaced apart and remain aligned in the proper coordinate system relative to the lower frame portion.

In a preferred embodiment of the invention there is a vertical cut (groove) on the rear side of the block of the upper frame which receives a pivotable tongue secured to the crossbar of the lower frame to exclude transverse (axial) shifting of the ball sockets on the balls in case of individually shaped guide means.

According to the invention, novel mounting plates are provided which have raised portions in the non-contacting regions of the planar contact surfaces contacting the lower frame or the upper frame, respectively. Said raised portions particularly serve to protect the upper planar contact surfaces against soiling, e.g. when put down on the working table, and may be supporting ledges or preferably cylindrical supporting lugs. In the latter case mounting plates are preferred which additionally have matching holes for receiving the supporting lugs in the side opposite said supporting lugs, e.g. at the below described dovetail-shaped webs, and a honeycomb structure in the region facing the upper frame portion and/or the lower frame portion after assembly.

The cylindrical supporting lugs and the matching holes may, of course, have any other desired structure, e.g. quadrangular or hexagonal or conical. Also the honeycomb structure may be round or non-round, e.g. triangular, quadrangular (square or rectangular) or hexagonal.

According to the invention, it has further been found that it is advantageous when one of the two cylindrical depressions in the mounting plates is designed as an elongated hole with elastic walls separated from the ribs by recesses, the space between the two elastic walls of the elongated hole being somewhat less than the diameter of the supporting lug extending into the elongate hole after mounting.

Preferably the mounting plates of the invention additionally have dovetail-shaped webs of the side facing the jaw model to assist in and to facilitate plaster-mounting of the jaw models. The webs may be lower in the rear half of the mounting plate than in the front region of the mounting plate.

The raised portions and/or the dovetail-shaped webs may be additionally provided at conventional mounting plates, or they may be cast or injection molded integrally therewith from the first.

Another feature of the invention may be seen in the rearwardly highly raised confining wall of the preferably circular planar supporting platform for the incisor guiding pin. The confining wall prevents the escape of the soft material which is shaped in response to the motions of the incisor guiding pin.

According to the invention, a protective covering has been developed which consists, for instance, of a plastic film and has a hole which permits the protective cover to be placed around the screw-on mounting plates prior to plaster-mounting of the jaw model such that the cover substantially extends around the plates. In this way soiling of the articulator by outflowing plaster during mounting of the jaw models is prevented.

According to the invention, an attachment was designed which, during the practical use of articulators, permits firm connection between articulator and transmission system. This attachment consists of a block with a horizontal slot in its base portion and adapted for plug connection and with a horizontal bore for receiving the axially slidable arm with a spindle. Preferably the attachment of the invention has at least two superposed bores for receiving the axially slidable arm with a spindle. The length of the spindle generally depends on the number of horizontal bores. Owing to the rigid connection between the articulator and the transmission system by means of the attachment of the invention, the transmission sheet can be adjusted in the articulator without any displacement.

Further details and features of the invention will become apparent from the following description in conjunction with the attached drawings. The drawings by means of which the invention will be further explained illustrate only preferred embodiments of the dental articulator of the invention. Therefore, the invention is not restricted to these preferred embodiments.

Figure 1:
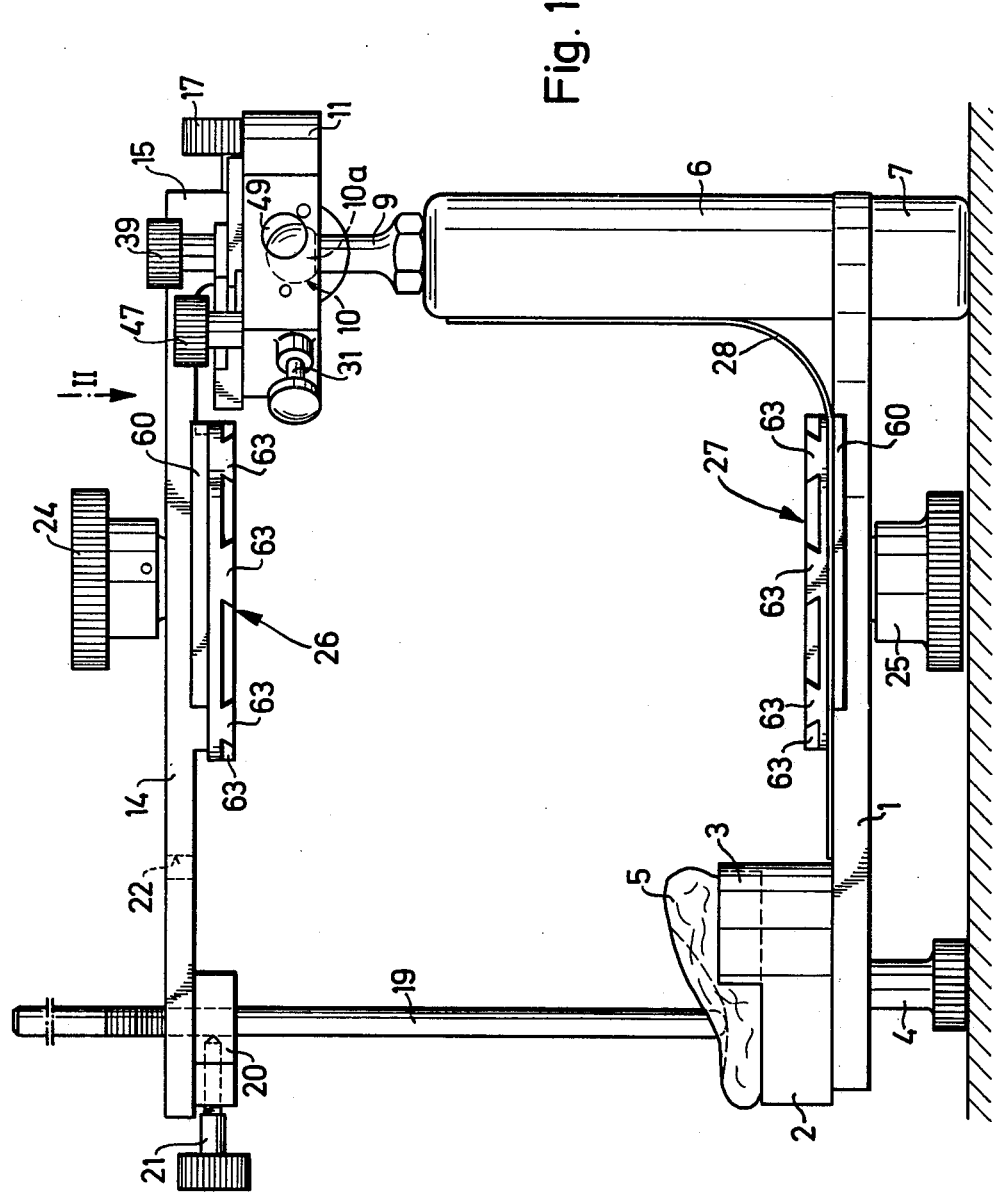
FIG. 1 shows a lateral view of an articulator according to the invention.
Figure 2:
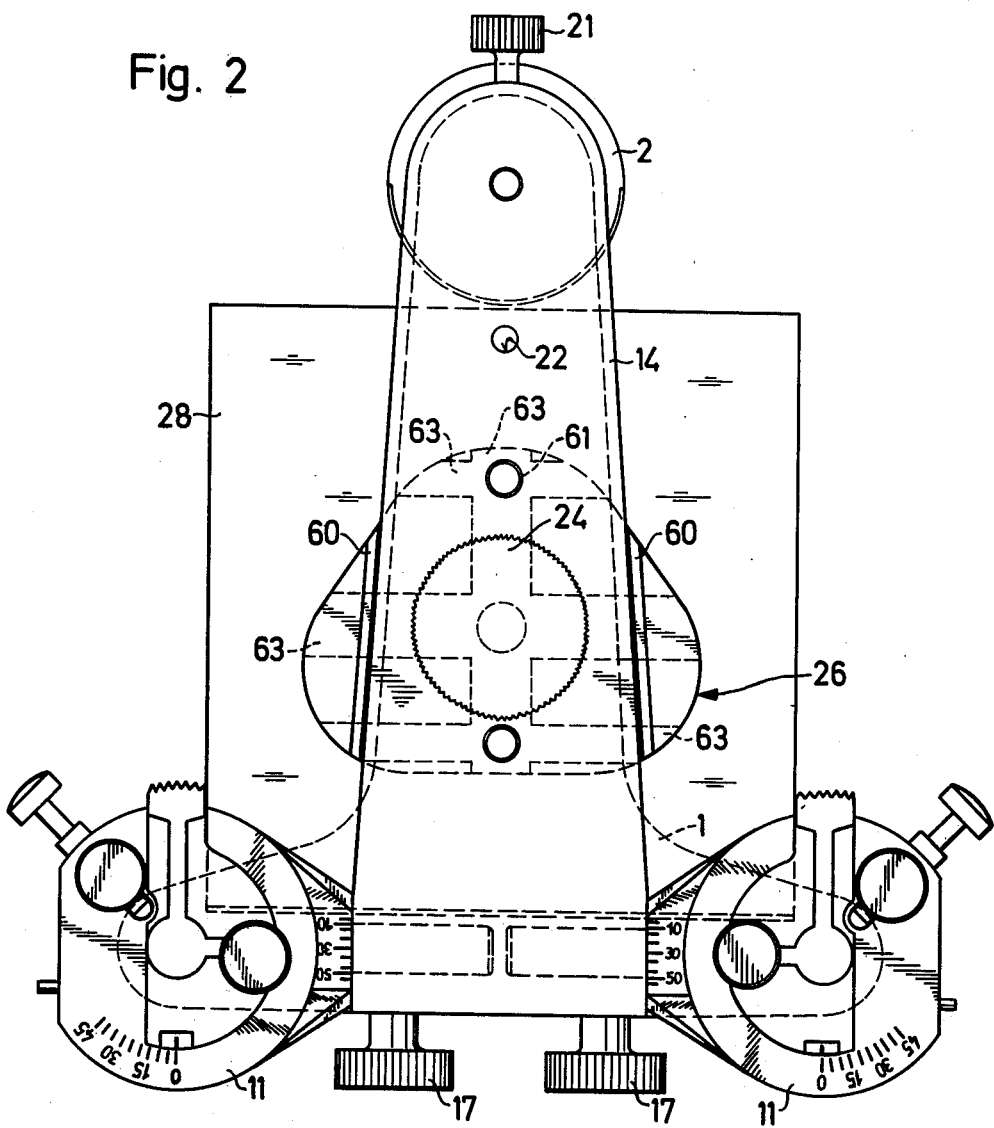
FIG. 2 is a top view of the articulator of the invention (plan view).

From FIG. 1 it is apparent that the dental articulator of the invention consists of a lower frame 1 whose precise configuration is shown in FIG. 2 by the broken lines. In the forward part of the lower frame 1 there is a planar supporting platform 2 with the raised confining wall 3. The supporting platform which has a guide jaw with threaded sleeve in the center of its underside is rigidly connected to the lower frame portion 1 by means of screw 4. The screw 4 simultaneously serves as forward foot of the articulator. On the supporting platform 2 a soft moldable material 5 may be applied for visualizing patterns of motion, which hardens after impression of the patterns.

Figure 7:
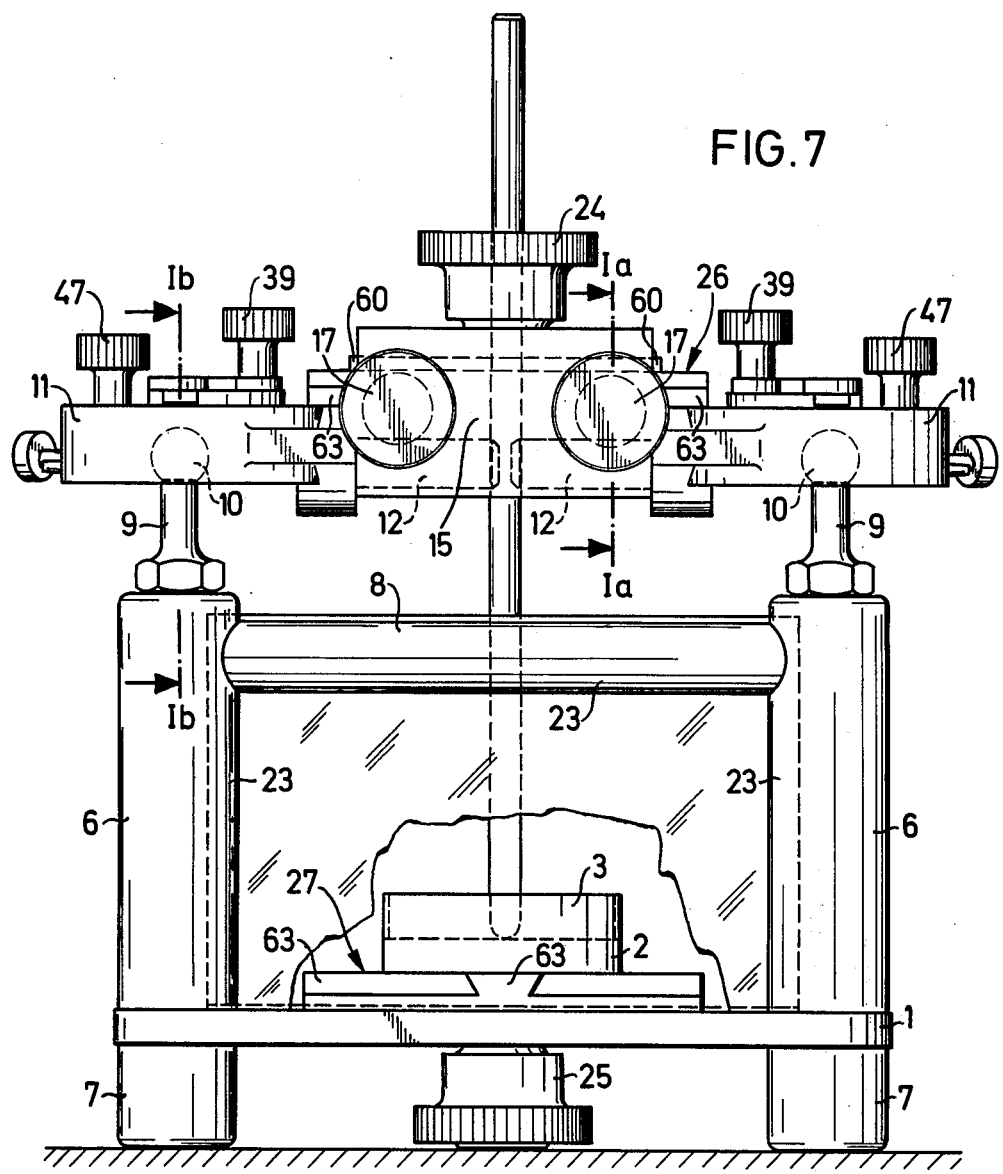
FIG. 7 shows the articulator of the invention from the back side (rear view).

At the rear end of the lower frame 1 there are the supporting pillars 6 forming the vertical frame 23 and being rigidly screwed below to the rear articulator feet 7 so as to grip the lower frame 1 between them. Into the supporting pillars which are interconnected on top by the crossbar 8 shown in FIG. 7 in a precisely predetermined distance the supporting stems 9 are screwed with the balls 10 serving as condyles.

Figure 7A:
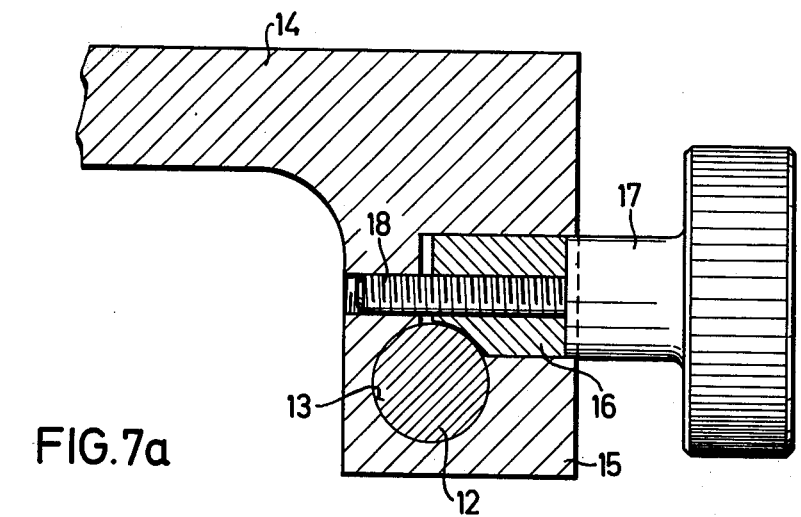
FIG. 7a is a section along line Ia—Ia in FIG. 7.

On the balls 10 there rest the ball sockets 11 serving as fossae which extend with their bearing shafts 12 into the bearing bores 13 serving as bearing guide of the transverse block 15 shown in FIG. 7a in section and forming a unit with the upper frame 14. In said bearing bores said sockets are locked by means of the cylindrical clamping means 16 in combination with the locking screw 17 whose threaded shank 18 extends through the clamping means 16 and is screwed into a threaded sleeve (not shown) located in the transverse block 15 above the bearing bore 13 (see FIG. 7a).

At the upper end of the upper frame 14 the incisor guiding pin 19 is mounted in a bore extending through the upper frame 14 and through a locking means 20 rigidly connected to the latter. The incisor guiding pin 19 is locked by a simple locking screw 21; in the region where normally it is locked the incisor guiding pin is preferably grooved to exclude maladjustment in height during operation.

In the forward part of the upper frame 14 there is also a hole 22 for the reference indicator to determine the reference plane.

Centrally at the upper frame 14 and at the lower frame 1 mounting screws 24 and 25 are provided for detachably connecting the mounting plates 26 and 27 (FIG. 1). The latter permit mounting of the upper and lower jaw models to the upper 14 and the lower frames 1.

Figure 9:
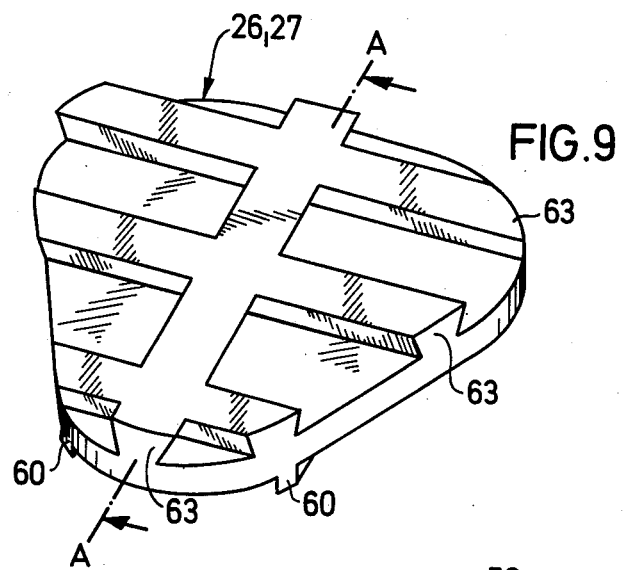
FIG. 9 shows the mounting plate of the invention from top in perspective view.
Figure 10:
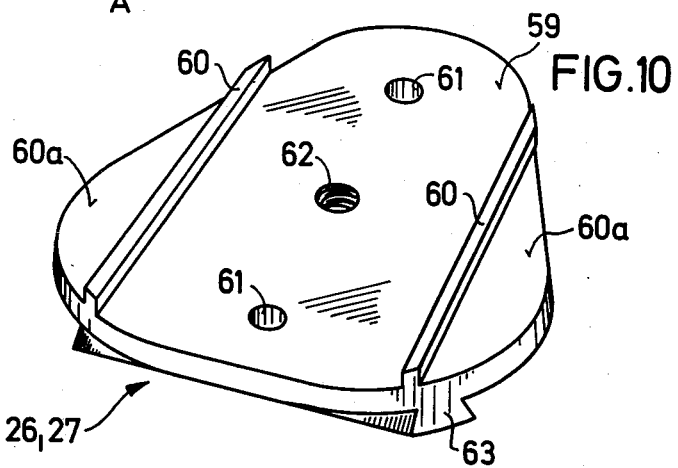
FIG. 10 shows the mounting plate of the invention from below in perspective view.
Figure 11:
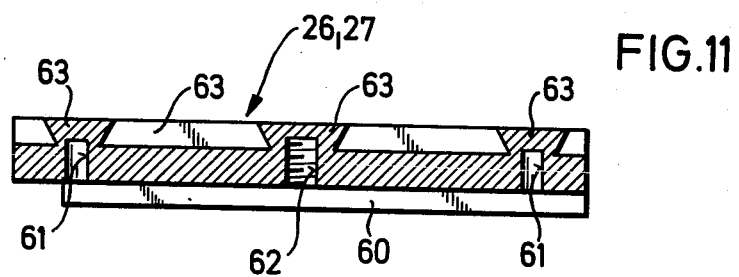
FIG. 11 shows a section along line A—A in FIG. 9.

From FIGS. 9 to 10 it is apparent that the mounting plates 26 and 27 have supporting ledges 60 on their lower surface, i.e. the contact surface 59. The width of the supporting ledges 60 is variable, optionally they may extend to the outer edge, i.e. they may cover the surfaces 60a. In lieu of the supporting ledges 60 also raised portions of the form of small lugs or the like may be provided. The cylindrical depressions 61 in the contact surface 59 and the threaded bore 62 have the conventional dimensions. On the upper sides of the mounting plates there are the dovetail-shaped webs 63.

Figure 12:
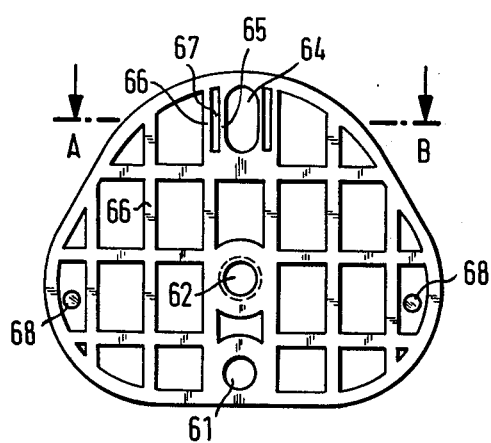
FIG. 12 is a plan view of the mounting plate of the invention from below.
Figure 13:
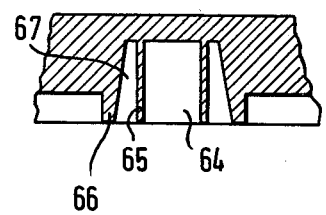
FIG. 13 shows an enlarged section along line A-B in FIG. 12.
Figure 14:
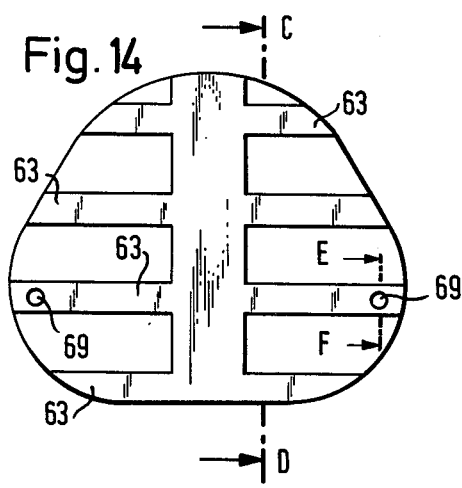
FIG. 14 shows a plan view of the mounting plate of the invention from top.
Figure 15:
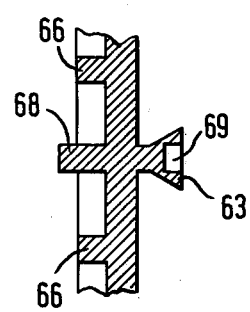
FIG. 15 shows an enlarged section along line E-F in FIG. 14.
Figure 16:
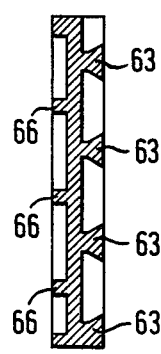
FIG. 16 shows a section along line C-D in FIG. 14.

According to the preferred embodiment of the invention, the supporting ledges 60 are replaced by the supporting lugs 68 (see FIGS. 12 and 15). The supporting lugs 68 are designed such that they fit into the holes 69 (see FIGS. 14 and 15) when the mounting plates are stacked.

Moreover, the undersides of the mounting plates, i.e. the contact areas 59 and the areas 60a, have a honeycomb structure on account of the longitudinal and transverse ribs 66.

The elongated hole 64 shown in FIG. 12 has elastic walls 65 on the longitudinal sides which are separated from the ribs 66 by recesses 67. Of course, also the cylindrical depression 61 in FIG. 12 could be designed as elongate hole 64 and the elongate hole 64 could be cylindrical depression instead.

The mounting plate 27 is surrounded by the protective cover 28.

The ball socket 11 serving as fossa is characterized by the circular inner cavity, by the inner ball guiding means 30 angularly adjustable relative to the rear ball guiding means 29, and by the lockable slide 31. The angularly adjustable inner ball guiding means 30 is an exchangeable segment of a circle optionally grindable to meet individual needs which bears against the circular inner wall 32 of the ball socket 11 and is rigidly connected to a threaded pin 33. Said threaded pin extends through an arcuate slot 34 in the upper ball guiding surface 35 and through the hole 36 of the turnable semi-disk 37 provided with a nonius with turning handle 38 so that the inner ball guiding means can be locked in any desired angular position by fastening the locking nut 39. The selected angular position may be seen from dial 40. In the turnable semi-disk 37 there is a blind hole 41 into which a matching cylindrical protrusion 42 provided at the upper side of the ball socket 11 extends about the semi-disk 37 is rotatable.

Figure 6:
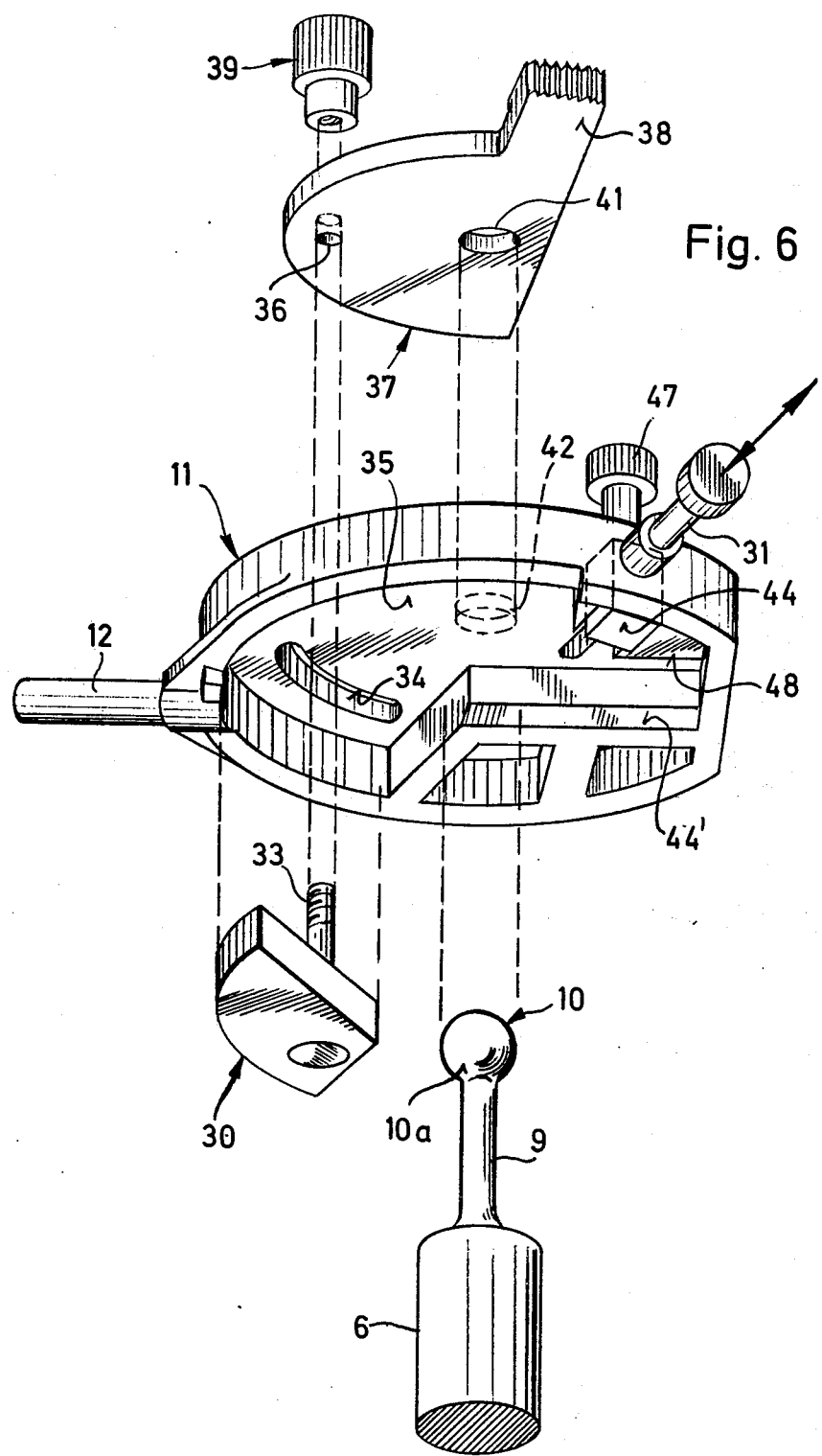
FIG. 6 is a perspective exploded view of the ball socket of the invention from below.

The angularly adjustable inner ball guiding means 30 designed as segment of a circle may consist of a solid or a perforated piece of material, e.g. provided with a web, as shown for the rear ball guiding means 29 in FIG. 6.

Figure 7B:
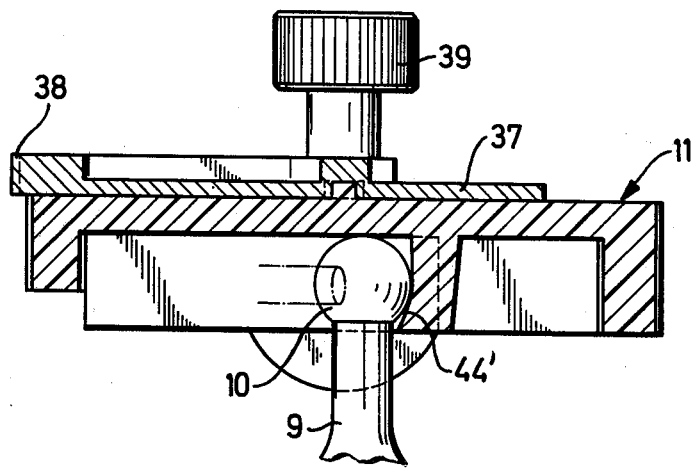
FIG. 7b is a section along line Ib—Ib in FIG. 7.

The guide wall 43 of the rear ball guiding means 29 has a slope 44 (FIG. 7b) which, when extrapolated to the upper guide surface, forms with the said upper guide surface an angle of less than 90°, preferably an angle of 60°. The slope 44 may extend up to the upper guide surface.

The ball 10 serving as condyle is locked by the lockable slide 31 which is rigidly connected to a cubic guide member 44' provided with a threaded pin 45. The threaded pin 45 extends through an elongate hole 46 in the upper side of the ball socket 11 and out of the ball socket. The slide 31 can be locked in the desired position by fastening the locking nut 47.

The diameters of the threaded pins 45 and 33 are preferably dimensioned such that they nearly contact the walls of the elongate hole 46 and the arcuate hole 34, respectively. In this way the threaded pins 45 and 33 simultaneously serve as guide pins for the slide 31 and for the angularly adjustable inner ball guiding means 30.

Moreover, or in lieu of the guidance by the threaded pin 45, the slide 31 may be guided by guide jaws 48 in cooperation with the cubic guide portion 44'.

The hole 49 serving as observation aperture and shown in FIG. 1 may be more or less large bore or a real window.

Figure 3:
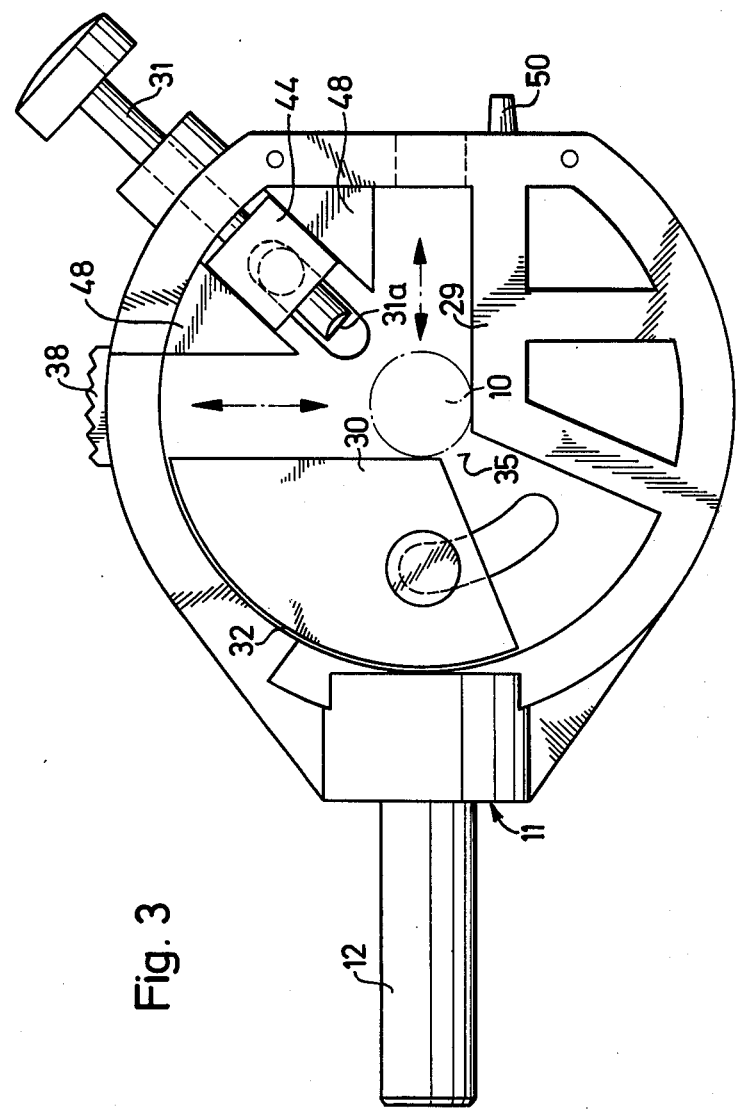
FIG. 3 shows the ball socket of the invention from below on enlarged scale.
Figure 4:
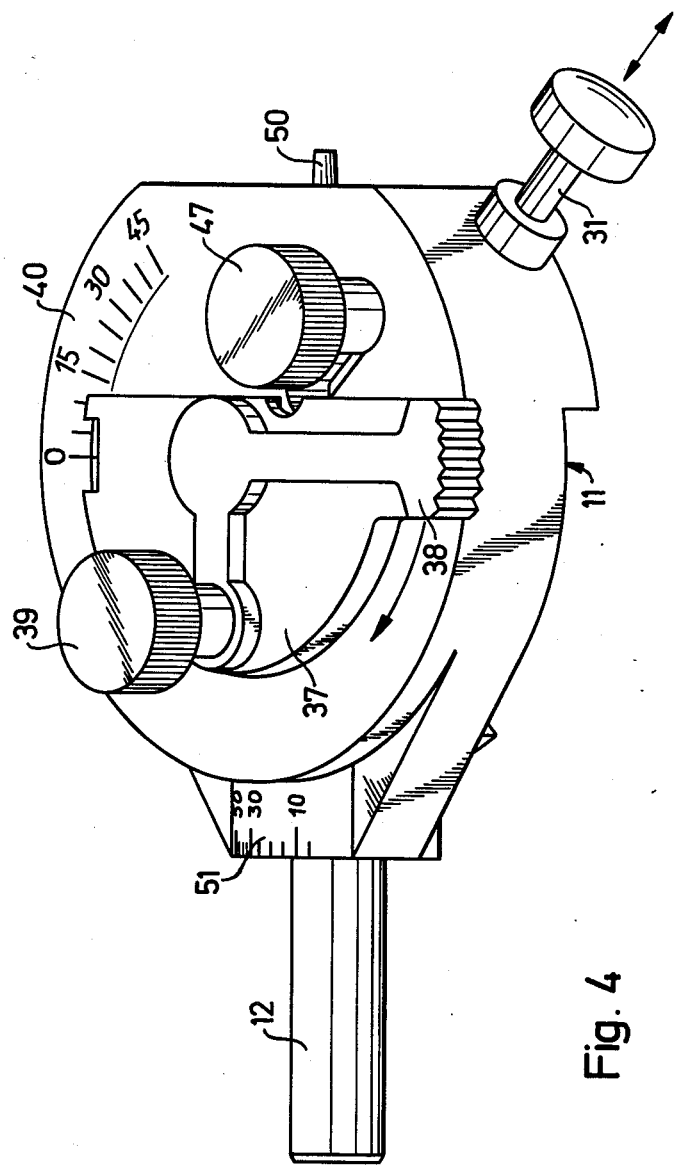
FIG. 4 shows the ball socket of the invention from top in perspective view on an enlarged scale.
Figure 5:
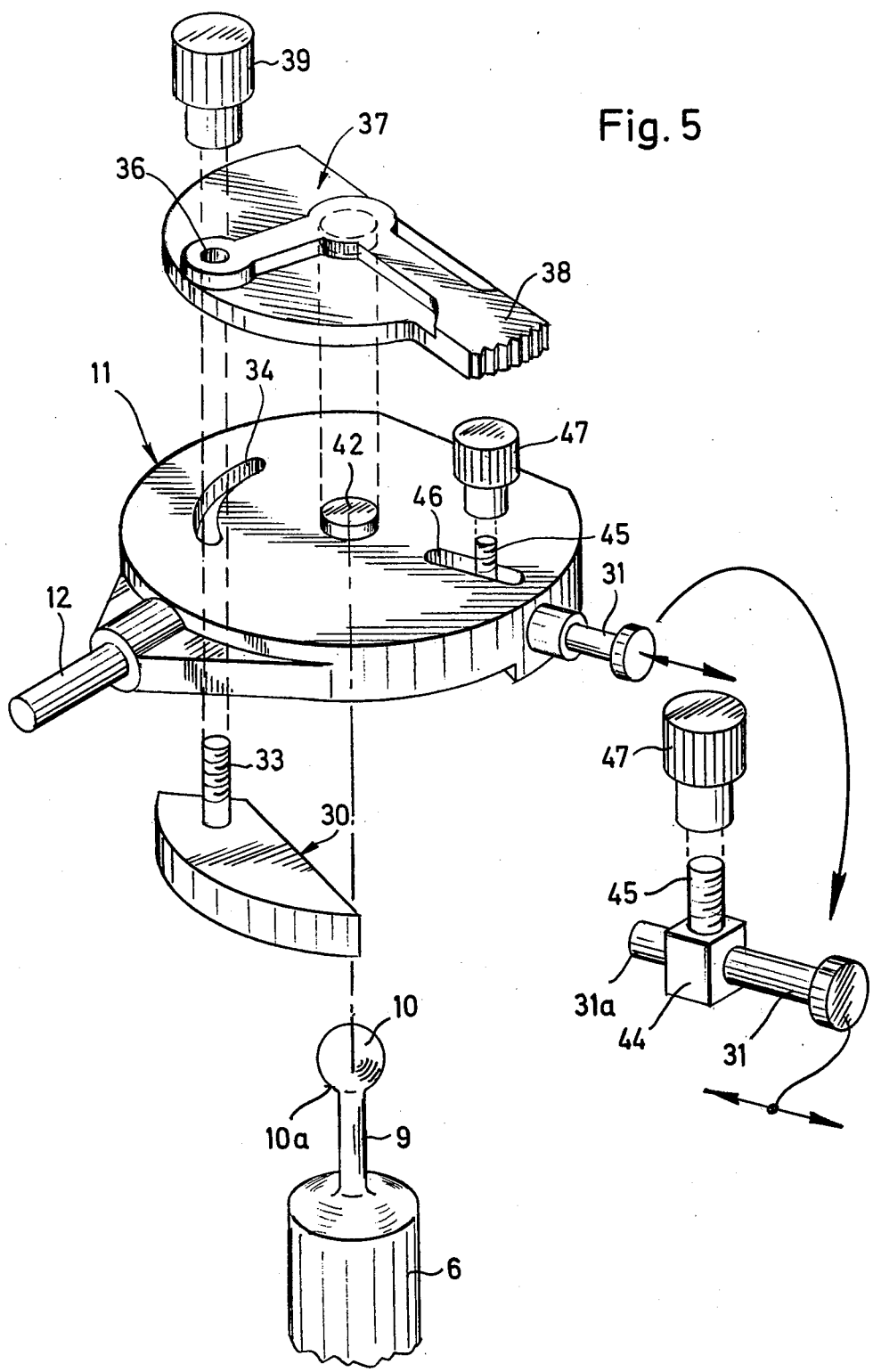
FIG. 5 is a perspective exploded view of the ball socket of the invention from top.

The small lugs 50 visible in FIGS. 2, 3 and 4 serve to suspend a transmission system.

The adjustment of the angle of inclination of the ball socket 11 takes place by rotation of the bearing shaft 12 about its longitudinal axis. The angle of inclination may then be read from the entrained dial 51.

Figure 8:
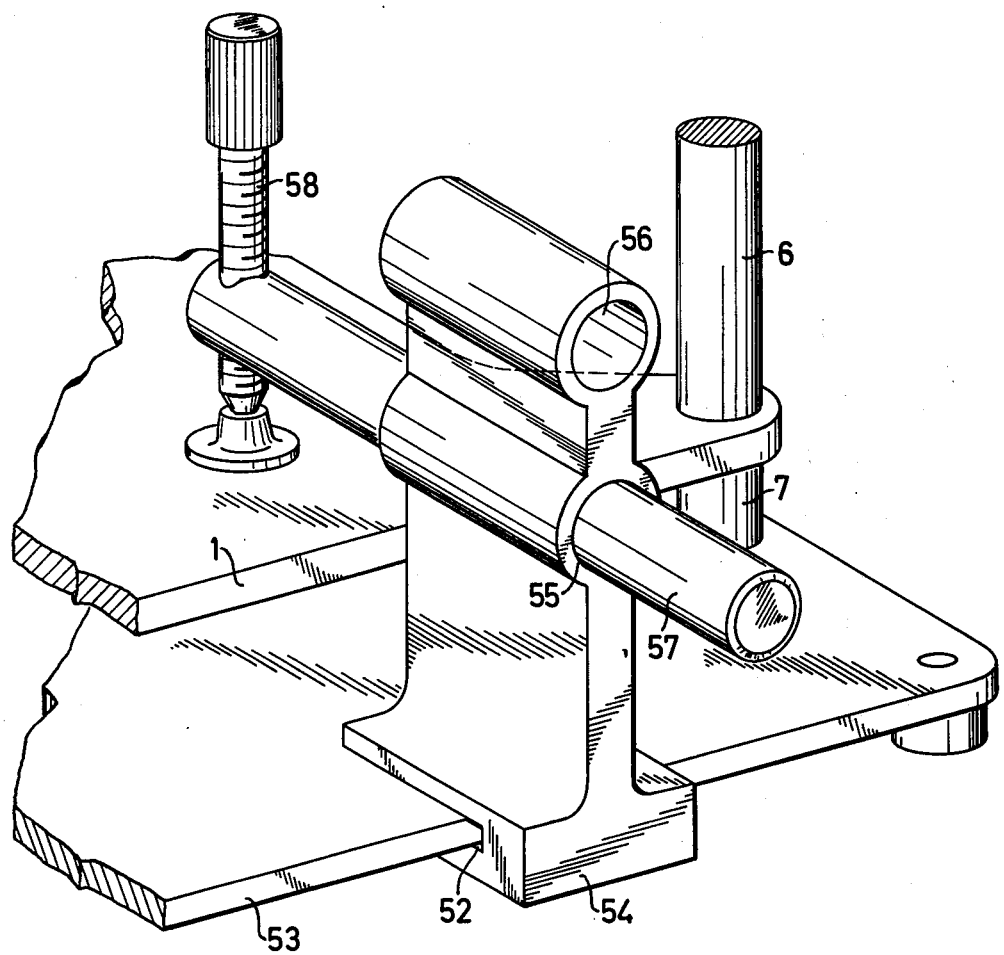
FIG. 8 shows the attachment means of the invention in perspective view.

The attachment means of the invention shown in FIG. 8 has in its base portion a horizontal slot 52 which permits sliding of the attachment means onto the base plate 53 of the transmission system. Above the base portion 54 provided with the horizontal slot there are two superposed bores 55 and 56. In the bore 55 there is the axially slidable arm 57 with spindle 58.

What is claimed is:

1. A dental articulator comprising a lower frame portion with means for securing a mounting plate for the lower jaw model and a supporting platform or the incisor guide pin, a vertical frame portion rigidly connected to the lower frame portion and having two balls serving as condyles which are mounted on two supporting stems, and an upper frame portion with the two radially rotatable ball sockets serving as fossae and including a rear ball guiding means, and an inner ball guiding means which is angularly adjustable relative to the rear ball guiding means, a bearing shaft, means for securing a mounting plate for the upper jaw model to said upper frame portion, and an adjustable incisor guide pin, characterized in that the inner ball guiding means which is angularly adjustable relative to the rear ball guiding means comprises an exchangeable, optionally grindable segment of a circle bearing against a circular inner wall of the ball, and a lockable slide is provided which serves to lock the ball in the corner formed by the rear ball guiding means, the angularly adjustable inner ball guiding means, and an upper ball guiding surface, said slide being arranged opposite, or diagonally opposite, the corner formed by the rear ball guiding means and the angularly adjustable inner ball guiding means such that, after locking, one end of the slide rests on the lower half of the ball.

2. Dental articulator according to claim 1 characterized in that the ball socket has an aperture serving as observation window.

3. Dental articulator according to claim 1 characterized in that the upper frame portion includes a vertically downwardly extending transverse block with bearing bores spaced a specific distance below the plane of the upper frame portion and serving as bearing guides.

4. Dental articulator according to claim 1 characterized in that the bearing shafts of the ball sockets are locked in the bearing bores by means of a cylindrical clamping element which has a bore in its longitudinal axis and a concave bearing surface at the end contacting the bearing shaft with a radius of curvature conforming to that of the bearing shaft.

5. Dental articulator according to claim 1 characterized in that the vertical frame portion consists of swivels and the supporting pillars have been rigidly connected to a crossbar in a gauge at a reproducible distance.

6. Dental articulator according to claim 1 characterized in that the planar supporting platform for the incisor guiding pin has a raised edge on one side thereof.

7. Dental articulator according to claim 1 characterized in that the mounting plates have raised portions in the regions of the surface that are not in contact with the lower frame portion and that upper frame portion, respectively.

8. Dental articulator according to claim 7 characterized in that the mounting plates have cylindrical supporting lugs on the surfaces thereof.

9. Dental articulator according to claim 8 characterized in that the mounting plates have dovetail-shaped webs on the sides thereof facing the jaw model.

10. Device according to claim 9 characterized in that on the dovetailed webs opposite the supporting lugs, matching holes (69) are provided for receiving the supporting lugs.

11. Device according to claim 1 characterized in that said mounting plates include a contacting surface and a further surface having a honeycomb structure.

12. Device according to claim 1 characterized in that one of two cylindrical depressions in the mounting plates is designed as an elongate hole with at least two elastic walls separated from ribs of the plates by recesses, the space between the two elastic walls of the elongate hole being somewhat less than the diameter of a supporting lug extending into the elongate hole after assembly.

13. An apparatus for providing a firm connection between a frame member of a dental articulator including a supporting foot and a base plate for a transmission system on which said supporting foot rests, said apparatus comprising a block member including a base portion having a slot therein in which the base plate of a transmission plate is received, said block member including at least one bore located above said slot, and said apparatus further comprising an axially movable arm received in said bore and a spindle, carried by said arm, for engaging the frame member of the dental articulator.

* * * * *